United States Patent [19]

Hayashi et al.

[11] Patent Number: 5,928,921
[45] Date of Patent: Jul. 27, 1999

[54] HUMAN FLAVIN-CONTAINING MONOOXYGENASE

[75] Inventors: Koji Hayashi; Yasushi Matsuki; Yoshiyasu Yabusaki, all of Hyogo, Japan

[73] Assignee: Sumitomo Chemical Company, Ltd., Osaka, Japan

[21] Appl. No.: 08/560,916

[22] Filed: Nov. 20, 1995

[30] Foreign Application Priority Data

Nov. 18, 1994 [JP] Japan .................................... 6-284902

[51] Int. Cl.$^6$ .............................. C12N 9/02; C07H 21/04
[52] U.S. Cl. ................. 435/189; 435/254.11; 435/252.3; 435/252.33; 435/320.1; 536/23.1; 536/23.2; 536/23.5
[58] Field of Search .................................. 435/189, 252.3, 435/252.33, 254.11, 320.1; 536/23.2, 23.5

[56] References Cited

PUBLICATIONS

Lomri et al., "Regio–Stereoselective Oxygenations by Adult Human Liver Flavin–Containing Monooxygenase 3. Comparison with Forms 1 and 2", *Chem. Res. Toxicol.*, 6:800–807, 1993.

Burnett et al., "Cloning and Sequences of Flavin–containing Monooxygenases FMO3 and FMO4 from Rabbit and Characterization of FMO3", *J. Biol. Chem.*, 269:14314–14322, 1994.

Lomri et al., "Molecular cloning of flavin–containing Monooxygenase (form II) cDNA from Adult Human Liver", *Proc. Natl. Acad. Sci.*, 92:9910, 1995.

Lomri et al., "Expression in *Escherichia coli* of the Flavin–Containing Monooxygenase D (Form II) from Adult Human Liver: Determination of a Distinct Tertiary Amine Substrate Specificity", *Chem Res. Tox.*, 6:425–429,1993.

Dolphin et al., "Differential developmental . . . FMO1, FMO3 and FMO4" Eur. J. Biochem. 235, 683, 1996.

Lawton, Michael P. and Philpot, Richard M., "Functional Characterization of Flavin–containing Monoxygenase 1B1 Expressed in *Saccharomyces cervisiae* and *Escherichia coli* and Analysis of Proposed FAD–and Membrane–binding Domains", *J. Biol. Chem.*, 268:8:5728–5734, 1993.

Lomri et al., "Molecular Cloning of the Flavin–containing Monooxygenase (Form II) cDNA from Adult Human Liver", *Proc. Natl. Acad. Sci. USA*, 89:1685–1689,1992.

Dolphin et al., "Cloning, Primary Sequence and Chromosomal Localization of Human FMO2, a New Member of the Flavin–Containing Mono–Oxygenase Family", *Biochem. J.*, 287:261–267, 1992.

Lawton et al., "A Nomenclature for the Mammalian Flavin–Containing Monooxygnease Gene Family Based on Amino Acid Sequence Identities", *Arch. Biochem. Biophys.*, 308:1:254–257, 1994.

Dolphin et al., "Cloning, Primary Sequence, and Chromosomal Mapping of a Human Flavin–Containing Monooxygenase (FMO1)", *J. Biol. Chem.*, 266:19:12379–12385, 1991.

*Primary Examiner*—Robert A. Wax
*Assistant Examiner*—Nashaat T. Nashed
*Attorney, Agent, or Firm*—Sughrue, Mion, Zinn Macpeak & Seas, PLLC

[57] ABSTRACT

A flavin-containing monooxygenase comprising the amino acid sequence of SEQ ID NO:8, a microorganism producing said flavin-containing monooxygenase, a flavin-containing monooxygenase gene containing a DNA sequence coding for the amino acid sequence of SEQ ID NO:8, a flavin-containing monooxygenase gene containing the DNA sequence of SEQ ID NO:7, a plasmid containing said flavin-containing monooxygenase gene, a microorganism containing said plasmid, and a method for producing the enzyme of the present invention wherein said microorganism is cultured to produce the enzyme.

11 Claims, 1 Drawing Sheet

# HUMAN FLAVIN-CONTAINING MONOOXYGENASE

FIELD OF THE INVENTION

The present invention relates to a novel human flavin-containing monooxygenase (FMO) gene.

DESCRIPTION OF THE PRIOR ART

Flavin-containing monooxygenases of rat, pig and rabbit are known as microsomal xenobiotic-metabolizing enzymes which oxidize various xenobiotics including drugs, agricultural chemicals and environmental pollutants. Some flavin-containing monooxygenases are characterized by a plurality of isozymes. Therefore, the precise characterization of and specific function of each enzyme molecule are not understood well. Particularly with regard to human flavin-containing monooxygenases, only 3 human flavin-containing monooxygenases have been elucidated by cDNA cloning (Dolphin et al., J. Biol. Chem., 266, 12379–12385, (1991), Dolphin et al., Biochem. J., 287, 261–267 (1992), Lomri et al. Proc. Natl. Acad. Sci. 89,1685–1689 (1992)). Therefore, many aspects of human flavin-containing monooxygenases, such as population distribution and characterization of function to metabolize or to detoxify xenobiotics, remain unknown.

Under the circumstances, the present inventors found a novel human flavin-containing monooxygenase and produced in a large quantity a functional human flavin-containing monooxygenase by a DNA amplification technique using particular oligonucleotides as primers.

SUMMARY OF THE INVENTION

Thus, the present invention provides nucleotide sequences encoding a human flavin-containing monooxygenases, wherein the nucleotide sequences are RNA and DNA sequences, such as a flavin-containing monooxygenase gene containing a DNA sequence coding for the amino acid sequence of SEQ ID NO:8, a flavin-containing monooxygenase gene containing the DNA sequence of SEQ ID NO:7 (hereinafter, referred to as the gene of the invention), a vector containing said flavin-containing monooxygenase gene (hereinafter, referred to as the vector of the invention), a host cell containing said vector, and a method for producing the enzyme of the present invention, which comprises culturing said host cell and recovering the enzyme produced thereby.

The host cell of the invention includes, but is not limited to, microorganisms such as yeast. The vector of the invention includes, but is not limited to, plasmid and phage vectors, such as a plasmid suitable for expression in yeast. The present invention also provides nucleotide sequences that hybridize to the above-mentioned nucleotide sequences and that encode an enzyme having the xenobiotic-oxidizing activity of a human flavin-containing monooxygenase. (By the term, "hybridization", it is intended to refer to conventional hybridization conditions and preferably to stringent hybridization conditions.)

The present invention provides a novel human flavin-containing monooxygenase, a host cell which produces said enzyme, a nucleotide sequence comprising said enzyme gene and nucleotide sequences hybridizing therewith, and a vector containing said nucleotide sequence. The expressed enzyme of the present invention is useful in evaluating human xenobiotic metabolism in vitro.

The present invention further provides an antibody, preferably monoclonal, which specifically binds to an epitope of the enzyme of the invention. The present invention further provides oligonucleotide probes which specifically bind the nucleotide sequence of the invention.

The present invention additionally provides a cell-free extract, preferably a microsomal fraction, prepared from a transformed host cell of the invention.

The present invention further provides a method for metabolizing a sample compound comprising preparing a mixture of the sample compound and the host cell or cell-free extract of the invention, incubating the mixture and, optionally analyzing the products obtained thereby.

The above and other objects, features, and advantages of the present invention will be better understood from the following detailed descriptions taken in conjunction with the accompanying drawing, which is given by way of illustration only and is not limitative of the present invention.

DESCRIPTION OF THE PREFERRED EMBODIMENTS

Figure 1:
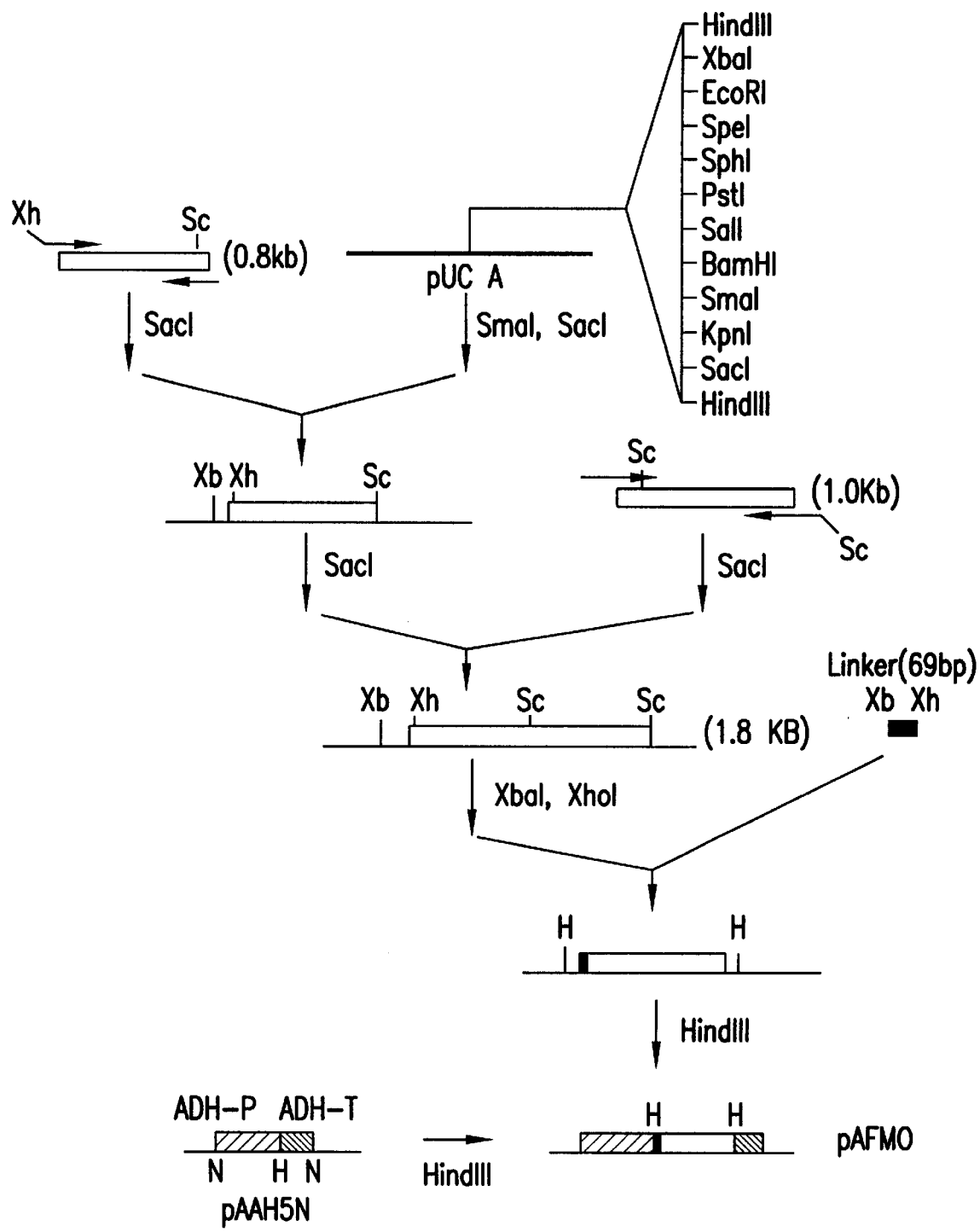
FIG. 1 depicts a construction method of a yeast expression plasmid (pAFMO) for a human flavin-containing monooxygenase.

According to the present invention, a novel human flavin-containing monooxygenase, antibodies thereto, a microorganism which produces said enzyme, said enzyme gene, and a plasmid containing said gene are obtained. The expressed enzyme of the present invention is useful to evaluate xenobiotic metabolism.

The invention now will be described in detail hereinbelow.

The enzyme of the present invention is novel and differs from any of the aforementioned three known human flavin-containing monooxygenases. The amino acid sequence of the instant enzyme or the DNA sequence coding for said polypeptide has about 50 to about 95% homology with the amino acid sequences or DNA sequences of the aforementioned known monooxygenases, respectively.

The gene of the present invention can be prepared by a conventional genetic engineering method, for example, cloning the subject gene from a cDNA library. The cDNA library can be obtained by preparing the mRNA fraction of suitable cells, producing cDNA therefrom using reverse transcriptase and inserting said cDNA into a vector, preferably a phage vector or a plasmid vector. Alternatively, a commercially available cDNA library derived from, for example, human liver can be employed. The library can be screened with either (i) a DNA fragment homologous to the gene or (ii) an antibody which binds to the instant enzyme. Furthermore, the gene can be prepared by amplifying and cloning the subject gene from a cDNA library by PCR using specific oligonucleotides as primers.

The DNA fragment for screening the library can be obtained by preparing deduced oligonucleotides based on the amino acid sequence of oligopeptides from the instant enzyme. Generally the deduced oligonucleotides comprise a family of possible sequences because of code degeneracy, however, it is not impossible to find oligopeptide fragments which would yield only one or two possible oligonucleotides which could encode such amino acid fragments.

The resulting oligonucleotides then can be labelled by conventional methods and used to screen the cDNA library to obtain clones carrying nucleotide sequences which encode portions or all of the instant enzyme.

Alternatively, the cDNA library can be screened by an antibody which binds the instant enzyme. The antibody can be polyclonal or monoclonal, made by standard techniques known in the art. Thus, a suitable host, such as a rodent is immunized with the instant enzyme, or portions thereof, using suitable diluents, routes and schedules as known in the art or which are optimized to obtain a suitable immune response thereto. At that point either serum, for polyclonal antisera, or splenocytes, for monoclonal antisera, are obtained.

Monoclonal antisera are developed using known techniques. The polyclonal and candidate monoclonal antibodies are screened for specificity, such as in an ELISA using the instant enzyme as the solid-phase bound analyte.

The relevant antibodies are used to screen the expression library. The antibodies can be used as labelled reagents or as unlabelled reagents. If unlabeled, an additional step wherein a labelled ligand which binds to the instant polyclonal or monoclonal antibody is used. Those reaction schemes will identify those clones which express protein which is bound by the instant antibodies specific for the instant enzyme.

Specific oligonucleotides which can be used as primers in a PCR include DNA fragments as set forth in SEQ ID NO's:1–4. When said primers are used, about a 1.6 kb fragment corresponding to the protein coding region of human flavin-containing monooxygenase gene, excluding 60 bp of N-terminal sequences, can be amplified separately as two fragments of about 0.8 kb and about 1.0 kb. The resulting two fragments, of about 0.8 kb and about 1.0 kb, and the fragment corresponding to the N-terminus of about 60 bp (linker) are ligated by a conventional genetic engineering method, thereby resulting in the gene of the present invention.

The vector of the present invention usually is constructed by inserting the gene of the present invention into an expression vector. The expression vector usually requires genetic information that enables replication in host microorganism cells, genetic information to enable independent propagation, characteristics which ensure ready isolation and purification from the host microorganism cells and further a detectable marker. Such a plasmid can be constructed by a conventional genetic engineering method or is available commercially.

In a yeast expression system, for example, a yeast expression plasmid can be prepared by inserting the gene of the present invention obtained by cloning same into an expression vector containing a promoter and terminator which are functional in yeast.

As a functional promoter in yeast, examples include promoters of a yeast alcohol dehydrogenase gene (hereinafter, referred to as an ADH promoter), of a glyceraldehyde-3-phosphate dehydrogenase gene (hereinafter, referred to as a GAPDH promoter) and of a phosphoglycerate kinase gene (hereinafter, referred to as a PGK promoter). The ADH promoter can be prepared, for example, from the yeast expression vector pAAH5 containing a yeast ADH1 promoter and terminator (available from Washington Research Foundation, Ammerer et al. Meth. Enzymol., 101, 192–201, U.S. Ser. No. 299,733 filed September, 1991) by a conventional genetic engineering method. Said yeast expression plasmid containing the aforementioned promoter and terminator which are active in yeast and the instant human flavin-containing monooxygenase gene can be constructed readily by a conventional genetic engineering methods. For example, the plasmid can be constructed by inserting the instant human flavin-containing monooxygenase gene into the HindIII sites of the yeast expression vector pAAH5N containing the ADH promoter and ADH terminator disclosed in JP-A No. 21180/1990.

The resulting vector of the present invention is introduced into host microorganism cells by a conventional method to produce a transformed host cell. Then, said host cells are cultured to produce the enzyme of the present invention selectively and in large quantity.

For example, a plasmid of the present invention is introduced into yeast, such as Saccharomyces cerevisiae, using known methods, such as an alkali metal (LiCl) method. The yeast into which said plasmid is introduced then is cultured by a conventional method to produce the enzyme of the present invention.

The recombinant vector and the polynucleotide of interest can be either RNA or DNA so long as the relevant polynucleotides can be used to identify or to express the gene or enzyme of interest.

The expressed enzyme generally is localized in the microsomal membrane where monooxygenase activity occurs. Therefore, the expressed enzyme can, for example, be used to investigate metabolism of a xenobiotic in vitro, preferably in the form of intact yeast cells or cell-free extracts. The xenobiotic can be a toxic substance, carcinogen or mutagen, or can be a compound which can be converted to a toxic substance, carcinogen or mutagen, for example, in vivo. Thus the instant enzyme can be used to test the xenobiotic or product thereof for any adverse characteristics.

As the cell-free extract, for example, a microsomal fraction of transformed cells can be used. Preparation of the cell-free extract or the microsomal fraction may be performed according to a conventional method described, for example, in DNA, 4(3):203–210 (1985).

The yeast cells or the cell-free extract thus obtained may be used to analyze a metabolic pathway of a sample compound by reacting the sample compound with the yeast cells or the cell-free extract. The reaction can be performed by adding the sample compound to a culture of the yeast cells or to a solution of cell-free extract, such as culture medium or buffer containing the yeast cells or the cell-free extract, and by incubating the reaction mixture, for example, at a temperature of about 10 to about 40° C., for about 0.1 to about 48 hours. The amount of the yeast cells or said cell-free extract and the amount of the sample compound to be added to the reaction mixture may be varied according to various conditions such as the reaction temperature, reaction time and the type of the sample compound. For example, the amount of the yeast cells or said cell-free extract is preferably between about $10^7$ and about $10^8$ cells, or about 5 to about 200 µl of the microsomal fraction (per 1 ml of the solution), and the amount of the sample compound to be added to the reaction mixture is preferably between about 0.01 and about 1 µmole per 1 ml of the solution. The amounts optionally can be increased or decreased as desired.

After completion of the reaction, analysis of the products and metabolites in the reaction solution can be conducted according to a conventional analytical method, as described in Guideline of Instrumental Analysis (New edition, first published 1985, KAGAKU-DOJIN Publishing Company, edited by Jiro Shiokawa et al.) or Spectrometric Identification of Organic Compounds (Fourth edition, third published 1984, TOKYO KAGAKU DOJIN Co., Ltd., edited by R. M. Silver et al.). As used herein, "metabolites" is meant to encompass any product resulting from an action of the instant enzyme.

Alternatively, the resulting products can be tested, for example, for toxicity or transforming activity in standard assays and bioassays, using for example, cell lines and organisms as test systems for such assessments. As used herein, "toxicity", is meant to encompass compounds which have a harmful effect on a cell, organism and the like. Thus, for example, a carcinogen or a mutagen is toxic.

On the basis of the data obtained, it can be judged as to whether the sample compound either is detoxified or activated to a harmful compound by the present enzyme.

The invention will be illustrated further with reference to the following examples; however, the examples are not to be construed to limit the scope of the invention.

EXAMPLE 1 (Method for obtaining the gene of the invention)

Using the primers of SEQ ID NO's:1 to 4, about a 1.6 kb fragment corresponding to the protein coding region of human flavin-containing monooxygenase without 60 bp of N-terminal sequence was amplified separately as two fragments of about 0.8 kb and about 1.0 kb, using PCR. The amplified fragment of about 0.8 kb was cleaved with SacI and subcloned into the SmaI-SacI site of the pUC A vector, which was prepared by modifying the EcoRI site of pUC19 (TAKARA SHUZO) into a HindIII site, and by converting the cloning sites between the HindIII sites into the following cloning sites:

The obtained subclone was treated with SacI and ligated to the fragment of about 1.0 kb which was pretreated with SacI, and then, the resulting plasmid was treated further with XbaI and XhoI into which the linkers of SEQ ID NO's:5 and 6 were inserted (see FIG. 1). The gene corresponding to the protein coding region of human flavin-containing monooxygenase was sequenced using a fluorescence DNA sequencer (model 373A, Applied Biosystems) which is based on the dideoxy method. The result is shown in SEQ ID NO:7, accompanied by the deduced amino acid sequence shown in SEQ ID NO:8.

EXAMPLE 2 (Construction of the plasmid of the invention)

The gene corresponding to the protein coding region of human flavin-containing monooxygenase was prepared by cleaving the obtained plasmid with HindIII, and inserting same into pAAH5N, whereby the yeast expression plasmid pAFMO was constructed, which allowed the gene of the invention to be expressed in yeast (see FIG. 1).

EXAMPLE 3 (Production of the microorganism of the invention)

Saccharomyces cerevisiae AH22 was inoculated in 1 ml of YPD medium (1%(w/v) yeast extract, 2%(w/v) polypeptone, and 2%(w/v) glucose), cultivated at 30° C. for 18 hours, and then collected by centrifugation (10,000×g, 2 minutes, room temperature). The obtained cells were suspended in 1 ml of 0.2 M LiCl solution, then centrifuged again, and to the resulting pellet were added 20 μl of 1 M LiCl, 30 μl of 70%(w/v) polyethyleneglycol 4000 solution and 10 μl of the solution containing about 1.0 μg of the plasmid of the present invention (pAFMO) constructed in Example 2. The resulting solution was mixed thoroughly, then incubated at 30° C. for 1 hour, a further 140 μl of distilled water was added thereto and the mixture stirred. The solution was spread on the SD synthetic plate (2.0% (w/v) glucose, 0.67%(w/v) yeast nitrogen base without amino acid, 20 g/ml histidine, 2.0%(w/v) agar), incubated at 30° C. for 3 days, and the transformant containing the plasmid of the present invention (pAFMO) was obtained.

EXAMPLE 4 (Preparation of the microsomal fraction of yeast)

The microorganism of the present invention (a transformed yeast produced in Example 3) was collected from 3.8 liters of liquid medium in which the microorganism was cultured up to a density of about $1.0 \times 10^8$ cells/ml. The yeast cells were suspended in 400 ml of buffer A (10 mM Tris-HCl (pH 7.5), 2 M sorbitol, 0.1 mM DTT, 0.2 mM EDTA), and to the resulting solution was added 160 mg of Zymolyase 100 T, and incubated at 30° C. for 60 minutes. After suspending spheroplasts obtained by centrifugation (5,000× g, 10 minutes, 4° C.) in 100 ml of buffer A, the resulting solution was subjected to centrifugation (5,000×g, 10 minutes, 4° C.). After washing the spheroplasts by subjecting the solution to centrifugation again under the same conditions, the spheroplasts were suspended in 200 ml of the buffer (10 mM Tris-HCl (pH 7.5), 0.65 M sorbitol, 0.1 mM DTT), and disrupted by ultrasonication (50 W, 5 minutes, 0° C.). The supernatant obtained by centrifugation (9,000×g, 20 minutes, 4° C.) was referred to as yeast S-9 Mix fraction hereinafter. The fraction was centrifuged further (125,000× g, 70 minutes, 4° C.) to collect pellets, which then were suspended in 10 ml of 0.1 M phosphate buffer (pH 7.4) to obtain a microsomal fraction.

EXAMPLE 5 (Assay of thiourea S-oxygenase activity in the microsomal fraction of yeast which expresses the enzyme of the present invention)

The reaction was initiated by adding 200 μl of the microsomal fraction prepared in Example 4 and 25 μl of 120 mM thiourea to 2.5 ml of an assay solution (0.1 M potassium phosphate buffer, pH 7.5, 0.2 mM NADPH, 160 μM thiocholine, 100 units catalase, 2 mM benzylimidazole, 0.4 mM EDTA) previously warmed at 37° C. Then, 400 μl of the mixture were added to 40 μl of 3 M TCA every 3 minutes, the resulting mixture was left standing on ice, and then centrifuged to obtain 350 μl of a supernatant. To the supernatant were added 1 ml of 1 M potassium phosphate buffer (pH 7.5), 0.6 ml of water and 50 μl of 10 mM dithiobisnitrobenzoic acid for coloration. The decrease of thiocholine was measured at an absorption of 412 nm. Thiourea S-oxygenase activity was found in the yeast microsomal fraction expressing the present enzyme.

All references cited herein are incorporated by reference in entirety.

It will be evident that various changes and modifications can be made without deviating from the spirit and scope of the instant invention.

What we claim is:

1. An isolated polynucleotide encoding an enzyme with xenobiotic oxidizing activity of human flavin-containing monooxygenase consisting of:
   (a) a nucleotide sequence of SEQ ID NO:7; or
   (b) a nucleotide sequence coding for the polypeptide of SEQ ID NO:8.

2. The isolated polynucleotide of claim 1 which is DNA.

3. The isolated polynucleotide of claim 1 which is RNA.

4. A vector comprising the polynucleotide of any one of claims 1 to 3.

5. The vector of claim 4 which is a plasmid or a phage.

6. The vector of claim 4 which further comprises a promoter and a terminator operably linked to said polynucleotide.

7. A host cell containing the vector of claim 4.

8. The host cell of claim 7 which is a yeast cell.

9. A method for producing an enzyme with xenobiotic oxidizing activity of human flavin-containing monooxygenase, comprising:
   (a) culturing the host cell of claim 7; and
   (b) recovering isolated microsomes containing said monooxygenase so produced.

10. A cell-free extract containing human flavin-containing monooxygenase activity prepared from the host cell of claim 7.

11. The cell-free extract of claim 10 which is a microsomal fraction.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:1:

GTCTCGAGGA AGGACTGGAG CCCACCTGCT T                                      31

(2) INFORMATION FOR SEQ ID NO:2:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:2:

GCCACACAGA ATGCTTGCTG GGAGCTCATC A                                      31

(2) INFORMATION FOR SEQ ID NO:3:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:3:

GTTGCTCGTC ACTCGATTTG GAACCTTCCT C                                      31

(2) INFORMATION FOR SEQ ID NO:4:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:4:

AAGAGCTCAG CCCCTGTCTG GGTATTGTCA G                                      31

(2) INFORMATION FOR SEQ ID NO:5:

(i) SEQUENCE CHARACTERISTICS:
       (A) LENGTH: 69 base pairs
       (B) TYPE: nucleic acid
       (C) STRANDEDNESS: single
       (D) TOPOLOGY: linear -continued (ii) MOLECULE TYPE: other nucleic acid
   (A) DESCRIPTION: /desc = "Synthetic DNA"

(xi) SEQUENCE DESCRIPTION: SEQ ID NO:5:

```
CTAGAATGGG GAAGAAAGTG GCCATCATTG GAGCTGGTGT GAGTGGCTTG GCCTCCATCA    60

GGAGCTGTC                                                            69
```

(2) INFORMATION FOR SEQ ID NO:6:

(i) SEQUENCE CHARACTERISTICS:
      (A) LENGTH: 69 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic DNA"

(xi) SEQUENCE DESCRIPTION: SEQ ID NO:6:

```
TTACCCCTTC TTTCACCGGT AGTAACCTCG ACCACACTCA CCGAACCGGA GGTAGTCCTC    60

GACAGAGCT                                                            69
```

(2) INFORMATION FOR SEQ ID NO:7:

(i) SEQUENCE CHARACTERISTICS:
      (A) LENGTH: 1599 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1596

(xi) SEQUENCE DESCRIPTION: SEQ ID NO:7:

```
ATG GGG AAG AAA GTG GCC ATC ATT GGA GCT GGT GTG AGT GGC TTG GCC     48
Met Gly Lys Lys Val Ala Ile Ile Gly Ala Gly Val Ser Gly Leu Ala
 1               5                  10                  15

TCC ATC AGG AGC TGT CTC GAG GAA GGA CTG GAG CCC ACC TGC TTT GAG     96
Ser Ile Arg Ser Cys Leu Glu Glu Gly Leu Glu Pro Thr Cys Phe Glu
             20                  25                  30

AAG AGC AAT GAC ATT GGG GGC CTG TGG AAA TTT TCA GAC CAT GCA GAG    144
Lys Ser Asn Asp Ile Gly Gly Leu Trp Lys Phe Ser Asp His Ala Glu
         35                  40                  45

GAG GGC AGG GCT AGC ATT TAC AAA TCA GTC TTT TCC AAC TCT TCC AAA    192
Glu Gly Arg Ala Ser Ile Tyr Lys Ser Val Phe Ser Asn Ser Ser Lys
     50                  55                  60

GAG ATG ATG TGT TTC CCA GAC TTC CCA TTT CCC GAT GAC TTC CCC AAC    240
Glu Met Met Cys Phe Pro Asp Phe Pro Phe Pro Asp Asp Phe Pro Asn
 65                  70                  75                  80

TTT ATG CAC AAC AGC AAG ATC CAG GAA TAT ATC ATT GCA TTT GCC AAA    288
Phe Met His Asn Ser Lys Ile Gln Glu Tyr Ile Ile Ala Phe Ala Lys
                 85                  90                  95

GAA AAG AAC CTC CTG AAG TAC ATA CAA TTT AAG ACA TTT GTA TCC AGT    336
Glu Lys Asn Leu Leu Lys Tyr Ile Gln Phe Lys Thr Phe Val Ser Ser
            100                 105                 110

GTA AAT AAA CAT CCT GAT TTT GCA ACT ACT GGC CAG TGG GAT GTT ACC    384
Val Asn Lys His Pro Asp Phe Ala Thr Thr Gly Gln Trp Asp Val Thr
        115                 120                 125

ACT GAA AGG GAT GGT AAA AAA GAA TCG GCT GTC TTT GAT GCT GTA ATG    432
Thr Glu Arg Asp Gly Lys Lys Glu Ser Ala Val Phe Asp Ala Val Met
    130                 135                 140
```

| | | | | | | | | | | | | | | | | |
|---|---|---|---|---|---|---|---|---|---|---|---|---|---|---|---|---|
| GTT | TGT | TCT | GGA | CAT | CAT | GTG | TAT | CCC | AAC | CTA | CCA | AAA | GAG | TCC | TTT | 480 |
| Val | Cys | Ser | Gly | His | His | Val | Tyr | Pro | Asn | Leu | Pro | Lys | Glu | Ser | Phe | |
| 145 | | | | 150 | | | | | 155 | | | | | 160 | | |

```
GTT TGT TCT GGA CAT CAT GTG TAT CCC AAC CTA CCA AAA GAG TCC TTT      480
Val Cys Ser Gly His His Val Tyr Pro Asn Leu Pro Lys Glu Ser Phe
145             150                 155                 160

CCA GGA CTA AAC CAC TTT AAA GGC AAA TGC TTC CAC AGC AGG GAC TAT      528
Pro Gly Leu Asn His Phe Lys Gly Lys Cys Phe His Ser Arg Asp Tyr
                165                 170                 175

AAA GAA CCA GGT GTA TTC AAT GGA AAG CGT GTC CTG GTG GTT GGC CTG      576
Lys Glu Pro Gly Val Phe Asn Gly Lys Arg Val Leu Val Val Gly Leu
            180                 185                 190

GGG AAT TCG GGC TGT GAT ATT GCC ACA GAA CTC AGC CGC ACA GCA GAA      624
Gly Asn Ser Gly Cys Asp Ile Ala Thr Glu Leu Ser Arg Thr Ala Glu
        195                 200                 205

CAG GTC ATG ATC AGT TCC AGA AGT GGC TCC TGG GTG ATG AGC CGG GTC      672
Gln Val Met Ile Ser Ser Arg Ser Gly Ser Trp Val Met Ser Arg Val
    210                 215                 220

TGG GAC AAT GGT TAT CCT TGG GAC ATG TTG CTC GTC ACT CGA TTT GGA      720
Trp Asp Asn Gly Tyr Pro Trp Asp Met Leu Leu Val Thr Arg Phe Gly
225                 230                 235                 240

ACC TTC CTC AAG AAC AAT TTA CCG ACA GCC ATC TCT GAC TGG TTG TAC      768
Thr Phe Leu Lys Asn Asn Leu Pro Thr Ala Ile Ser Asp Trp Leu Tyr
                245                 250                 255

GTG AAG CAG ATG AAT GCA AGA TTC AAG CAT GAA AAC TAT GGC TTG ATG      816
Val Lys Gln Met Asn Ala Arg Phe Lys His Glu Asn Tyr Gly Leu Met
            260                 265                 270

CCT TTA AAT GGA GTC CTG AGG AAA GAG CCT GTA TTT AAT GAT GAG CTC      864
Pro Leu Asn Gly Val Leu Arg Lys Glu Pro Val Phe Asn Asp Glu Leu
        275                 280                 285

CCA GCA AGC ATT CTG TGT GGC ATT GTG ACC GTA AAG CCT AAC GTG AAG      912
Pro Ala Ser Ile Leu Cys Gly Ile Val Thr Val Lys Pro Asn Val Lys
    290                 295                 300

GAA TTC ACA GAG ACC TCG GCC ATT TTT GAG GAT GGG ACC ATA TTT GAG      960
Glu Phe Thr Glu Thr Ser Ala Ile Phe Glu Asp Gly Thr Ile Phe Glu
305                 310                 315                 320

GGC ATT GAC TGT GTA ATC TTT GCA ACA GGG TAT AGT TTT GCC TAC CCC     1008
Gly Ile Asp Cys Val Ile Phe Ala Thr Gly Tyr Ser Phe Ala Tyr Pro
                325                 330                 335

TTC CTT GAT GAG TCT ATC ATC AAA AGC AGA AAC AAT GAG ATC ATT TTA     1056
Phe Leu Asp Glu Ser Ile Ile Lys Ser Arg Asn Asn Glu Ile Ile Leu
            340                 345                 350

TTT AAA GGA GTA TTT CCT CCT CTA CTT GAG AAG TCA ACC ATA GCA GTG     1104
Phe Lys Gly Val Phe Pro Pro Leu Leu Glu Lys Ser Thr Ile Ala Val
        355                 360                 365

ATT GGC TTT GTC CAG TCC CTT GGG GCT GCC ATT CCC ACA GTT GAC CTC     1152
Ile Gly Phe Val Gln Ser Leu Gly Ala Ala Ile Pro Thr Val Asp Leu
    370                 375                 380

CAG TCC CGC TGG GCA GCA CAA GTA ATA AAG GGA ACT TGT ACT TTG CCT     1200
Gln Ser Arg Trp Ala Ala Gln Val Ile Lys Gly Thr Cys Thr Leu Pro
385                 390                 395                 400

TCT ATG GAA GAC ATG ATG AAT GAT ATT AAT GAG AAA ATG GAG AAA AAG     1248
Ser Met Glu Asp Met Met Asn Asp Ile Asn Glu Lys Met Glu Lys Lys
                405                 410                 415

CGC AAA TGG TTT GGC AAA AGC GAG ACC ATA CAG ACA GAT TAC ATT GTT     1296
Arg Lys Trp Phe Gly Lys Ser Glu Thr Ile Gln Thr Asp Tyr Ile Val
            420                 425                 430

TAT ATG GAT GAA CTC TCC TCC TTC ATT GGG GCA AAG CCC AAC ATC CCA     1344
Tyr Met Asp Glu Leu Ser Ser Phe Ile Gly Ala Lys Pro Asn Ile Pro
        435                 440                 445

TGG CTG TTT CTC ACA GAT CCC AAA TTG GCC ATG GAA GTT TAT TTT GGC     1392
Trp Leu Phe Leu Thr Asp Pro Lys Leu Ala Met Glu Val Tyr Phe Gly
    450                 455                 460
```

| | | | | | | | | | | | | |
|---|---|---|---|---|---|---|---|---|---|---|---|---|
| CCT | TGT | AGT | CCC | TAC | CAG | TTT | AGG | CTG | GTG | GGC | CCA | GGG | CAG | TGG | CCA | 1440 |
| Pro | Cys | Ser | Pro | Tyr | Gln | Phe | Arg | Leu | Val | Gly | Pro | Gly | Gln | Trp | Pro | |
| 465 | | | | 470 | | | | | 475 | | | | | 480 | | |

| GGA | GCC | AGA | AAT | GCC | ATA | CTG | ACC | CAG | TGG | GAC | CGG | TCG | TTG | AAA | CCC | 1488 |
| Gly | Ala | Arg | Asn | Ala | Ile | Leu | Thr | Gln | Trp | Asp | Arg | Ser | Leu | Lys | Pro | |
| | | | | 485 | | | | | 490 | | | | | 495 | | |

| ATG | CAG | ACA | CGA | GTG | GTC | GGG | AGA | CTT | CAG | AAG | CCT | TGC | TTC | TTT | TTC | 1536 |
| Met | Gln | Thr | Arg | Val | Val | Gly | Arg | Leu | Gln | Lys | Pro | Cys | Phe | Phe | Phe | |
| | | | 500 | | | | | 505 | | | | | 510 | | | |

| CAT | TGG | CTG | AAG | CTC | TTT | GCA | ATT | CCT | ATT | CTG | TTA | ATC | GCT | GTT | TTC | 1584 |
| His | Trp | Leu | Lys | Leu | Phe | Ala | Ile | Pro | Ile | Leu | Leu | Ile | Ala | Val | Phe | |
| | | 515 | | | | | 520 | | | | | 525 | | | | |

| CTT | GTG | TTG | ACC | TAA | | | | | | | | | | | | 1599 |
| Leu | Val | Leu | Thr | | | | | | | | | | | | | |
| | | 530 | | | | | | | | | | | | | | |

(2) INFORMATION FOR SEQ ID NO:8:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Lys Lys Val Ala Ile Ile Gly Ala Gly Val Ser Gly Leu Ala
 1               5                  10                  15

Ser Ile Arg Ser Cys Leu Glu Glu Gly Leu Glu Pro Thr Cys Phe Glu
             20                  25                  30

Lys Ser Asn Asp Ile Gly Gly Leu Trp Lys Phe Ser Asp His Ala Glu
         35                  40                  45

Glu Gly Arg Ala Ser Ile Tyr Lys Ser Val Phe Ser Asn Ser Ser Lys
     50                  55                  60

Glu Met Met Cys Phe Pro Asp Phe Pro Phe Pro Asp Asp Phe Pro Asn
 65                  70                  75                  80

Phe Met His Asn Ser Lys Ile Gln Glu Tyr Ile Ile Ala Phe Ala Lys
                 85                  90                  95

Glu Lys Asn Leu Leu Lys Tyr Ile Gln Phe Lys Thr Phe Val Ser Ser
            100                 105                 110

Val Asn Lys His Pro Asp Phe Ala Thr Thr Gly Gln Trp Asp Val Thr
        115                 120                 125

Thr Glu Arg Asp Gly Lys Lys Glu Ser Ala Val Phe Asp Ala Val Met
    130                 135                 140

Val Cys Ser Gly His His Val Tyr Pro Asn Leu Pro Lys Glu Ser Phe
145                 150                 155                 160

Pro Gly Leu Asn His Phe Lys Gly Lys Cys Phe His Ser Arg Asp Tyr
                165                 170                 175

Lys Glu Pro Gly Val Phe Asn Gly Lys Arg Val Leu Val Val Gly Leu
            180                 185                 190

Gly Asn Ser Gly Cys Asp Ile Ala Thr Glu Leu Ser Arg Thr Ala Glu
        195                 200                 205

Gln Val Met Ile Ser Ser Arg Ser Gly Ser Trp Val Met Ser Arg Val
    210                 215                 220

Trp Asp Asn Gly Tyr Pro Trp Asp Met Leu Leu Val Thr Arg Phe Gly
225                 230                 235                 240

Thr Phe Leu Lys Asn Asn Leu Pro Thr Ala Ile Ser Asp Trp Leu Tyr
                245                 250                 255
```

```
Val Lys Gln Met Asn Ala Arg Phe Lys His Glu Asn Tyr Gly Leu Met
            260                 265                 270

Pro Leu Asn Gly Val Leu Arg Lys Glu Pro Val Phe Asn Asp Glu Leu
            275                 280                 285

Pro Ala Ser Ile Leu Cys Gly Ile Val Thr Val Lys Pro Asn Val Lys
            290                 295                 300

Glu Phe Thr Glu Thr Ser Ala Ile Phe Glu Asp Gly Thr Ile Phe Glu
305                 310                 315                 320

Gly Ile Asp Cys Val Ile Phe Ala Thr Gly Tyr Ser Phe Ala Tyr Pro
                325                 330                 335

Phe Leu Asp Glu Ser Ile Ile Lys Ser Arg Asn Asn Glu Ile Ile Leu
            340                 345                 350

Phe Lys Gly Val Phe Pro Pro Leu Leu Glu Lys Ser Thr Ile Ala Val
            355                 360                 365

Ile Gly Phe Val Gln Ser Leu Gly Ala Ala Ile Pro Thr Val Asp Leu
370                 375                 380

Gln Ser Arg Trp Ala Ala Gln Val Ile Lys Gly Thr Cys Thr Leu Pro
385                 390                 395                 400

Ser Met Glu Asp Met Met Asn Asp Ile Asn Glu Lys Met Glu Lys Lys
            405                 410                 415

Arg Lys Trp Phe Gly Lys Ser Glu Thr Ile Gln Thr Asp Tyr Ile Val
            420                 425                 430

Tyr Met Asp Glu Leu Ser Ser Phe Ile Gly Ala Lys Pro Asn Ile Pro
            435                 440                 445

Trp Leu Phe Leu Thr Asp Pro Lys Leu Ala Met Glu Val Tyr Phe Gly
    450                 455                 460

Pro Cys Ser Pro Tyr Gln Phe Arg Leu Val Gly Pro Gly Gln Trp Pro
465                 470                 475                 480

Gly Ala Arg Asn Ala Ile Leu Thr Gln Trp Asp Arg Ser Leu Lys Pro
            485                 490                 495

Met Gln Thr Arg Val Val Gly Arg Leu Gln Lys Pro Cys Phe Phe Phe
            500                 505                 510

His Trp Leu Lys Leu Phe Ala Ile Pro Ile Leu Leu Ile Ala Val Phe
        515                 520                 525

Leu Val Leu Thr
        530
```